(12) United States Patent
O'Brien

(10) Patent No.: US 8,011,071 B2
(45) Date of Patent: Sep. 6, 2011

(54) LOCKABLE MOUNTING MECHANISM FOR A RESPIRATORY SYSTEM HEATER UNIT

(75) Inventor: James W. O'Brien, Alpharetta, GA (US)

(73) Assignee: Smiths Medical ASD, Inc., Rockland, MA (US)

( * ) Notice: Subject to any disclaimer, the term of this patent is extended or adjusted under 35 U.S.C. 154(b) by 965 days.

(21) Appl. No.: 11/927,044

(22) Filed: Oct. 29, 2007

(65) Prior Publication Data

US 2009/0108168 A1   Apr. 30, 2009

(51) Int. Cl.
*A45F 5/00*   (2006.01)
(52) U.S. Cl. ............ 24/597; 24/3 R; 224/272; 224/197; 224/904; 248/221.11; 248/222.11
(58) Field of Classification Search .................. None
See application file for complete search history.

(56) References Cited

U.S. PATENT DOCUMENTS

| | | | |
|---|---|---|---|
| 1,080,832 A | 12/1913 | Isidor | |
| 2,669,494 A * | 2/1954 | Lenz, Sr. ...................... 24/594.1 |
| 3,145,042 A * | 8/1964 | Bendi ......................... 294/82.33 |
| 3,878,589 A | 4/1975 | Schaefer | |
| 4,203,027 A | 5/1980 | O'Hare et al. | |
| 5,054,170 A | 10/1991 | Otrusina | |
| 5,201,858 A | 4/1993 | Otrusina | |
| 5,347,693 A * | 9/1994 | Otrusina ................... 24/573.11 |
| 5,529,060 A | 6/1996 | Salmon et al. | |
| 5,604,958 A | 2/1997 | Anscher | |
| 5,620,120 A | 4/1997 | Tien | |
| 5,943,473 A | 8/1999 | Levine | |
| 6,824,028 B2 * | 11/2004 | Mutai et al. .................... 224/271 |
| 6,988,497 B2 | 1/2006 | Levine | |
| 7,077,372 B2 * | 7/2006 | Moran ...................... 248/222.11 |
| 7,261,264 B2 * | 8/2007 | Moran ...................... 248/222.11 |
| 7,726,706 B2 * | 6/2010 | Moran .......................... 292/194 |

OTHER PUBLICATIONS

Manual for Fisher & Paykel Model Nos. MR700, MR720, MR730 Respiratory Humidifiers (Mar. 1998) (48 pages).
Technical Manual Fisher & Paykel Respiratory Humidifier Model Nos. MR700, MR720, MR730, MR 480 (Mar. 2001) (64 pages).
Allegiance Healthcare 510K No. K993833 for Airlife® Heated Ventilator and Anesthesia Breathing Circuits (5 pages) (Dec. 10, 1999).
Brochure for Hudson RCI Humid-Heat® (6 pages).
Operating Manual for Fisher & Paykel Model Nos. MR700, MR720, MR730 Respiratory Humidifiers (Mar. 1994) (46 pages).
Instruction Sheet for Airlife® Single Heated Adult Respiratory Circuit (2 pages) (date uncertain).

(Continued)

*Primary Examiner* — Jack W. Lavinder
(74) *Attorney, Agent, or Firm* — Wood, Herron & Evans, LLP

(57) ABSTRACT

A lockable mounting mechanism has a hitch portion and a receiver portion, the hitch portion having a hitch member, a locking member being rotatable between an unlocked position and a locked position, and a camming surface being rotatable with the locking member and the receiver portion having a channel, the hitch member of the hitch portion and the channel of the receiver portion sized to slidably receive the hitch member into the channel portion whereby to mount the hitch portion to the receiver portion, the receiver portion further having a reset surface positioned to engage the camming surface as the hitch member is slid into the channel when the locking member is out of the unlocked position, the camming surface and reset surface cooperating to automatically rotate the locking member toward the unlocked position as the hitch member is slid into the channel.

25 Claims, 4 Drawing Sheets

OTHER PUBLICATIONS

Cardinal Health RT110 Data for Circuits, reprinted from the internet Jun. 3, 2006 (2 pages).
Fisher & Paykel 900MR561 Temperature Probe Label (one page) (date uncertain).
Fisher & Paykel Airway Temperature Probes Instructions for Use (3 pages) (2003).
Cat. RT110 Insert for Airlife™ Adult Respiratory Circuit—Heated (one page) (undated).

* cited by examiner

LOCKABLE MOUNTING MECHANISM FOR A RESPIRATORY SYSTEM HEATER UNIT

FIELD OF THE INVENTION

The present invention relates generally to mounting mechanisms, and more particularly, to a mounting mechanism used for supporting a respiratory system heater unit.

BACKGROUND AND SUMMARY OF THE INVENTION

Patients who are unconscious or experiencing severe medical conditions may require that breathable gas such as oxygen, anesthetic gas and/or air be directed into the mouth, nose or airway to assist or facilitate breathing. Many respiratory systems include a humidification system to warm and impart humidity to the breathable gas before it is provided to the patient. The humidification system typically employs a chamber for holding water and a heater unit adapted to heat the chamber. The breathable gas passes through the chamber where it is heated and humidified and carried to a patient by an inspiratory limb of a breathing circuit, which may also include an expiratory limb to carry expelled air and other gas(es) from the patient back to the ventilator.

The chamber is typically disposable and may be selectively coupled to the heater unit in thermal communication with a heated plate thereof. The heater unit contains the necessary electrical and electronic components to regulate the temperature of the heated plate as well as heating circuits of the breathing circuit, if desired. The heater units can be quite heavy, but typically need to be mounted to a support, such as a pole or a ventilator used to drive the breathable gas into the chamber and on to the patient. A mounting mechanism, such as a hitch associated with the heater unit and a receiver associated with the support, may be employed to mount the heater unit. The hitch may be secured to the free end of a mounting bracket secured to the heater unit, with the receiver defining a keyway or channel configured to slidably receive the hitch therein.

While a hitch and receiver mounting mechanism is useful, there are situations where the hitch could come out of the receiver leading to unintended consequences. By way of example, while moving the support to which the heater unit is mounted, such as when moving a patient from one room to another, bumps or other obstacles may be encountered which might jar the hitch loose from the receiver. A locking mechanism could be associated with the mounting mechanism so as to secure the hitch in the receiver during use, thus avoiding undesired release of the hitch therefrom. However, a locking mechanism could also interfere with sliding the hitch into the receiver.

The present invention provides a lockable mounting mechanism which is adapted to avoid undesired release of the hitch from the receiver, but which does not interfere with sliding the hitch into the receiver. To that end, and in accordance with the principles of the present invention, a pivoting locking member is associated with the hitch which can pivot between a locked and an unlocked position, and further has associated therewith a camming surface positioned, when the locking member is out of the unlocked position, to engage against a reset surface of the receiver to be automatically pivoted into the unlocked position as the hitch is slid into the receiver. As a result, the mounting mechanism is provided with a locking mechanism to be secured in place during use, but which does not interfere with sliding the hitch into the receiver.

The camming surface may be defined on a cam member which rotates with the locking member. In the unlocked position of the locking member, the cam member is oriented such that the camming surface is inboard of the reset surface. As a result, the camming surface will pass by the reset surface of the receiver without impacting thereagainst as the hitch is slid into the receiver. The receiver may include a slot or opening sized to receive the cam member therein and supporting the reset surface such as along an edge thereof. If the locking member is not in the unlocked position, the camming surface will be outboard of the reset surface such that attempts to slide the hitch into the receiver will cause the camming surface to impact against the reset surface of the receiver. The camming surface and reset surface cooperate such that continued sliding of the hitch into the receiver will cause the cam member to rotate the camming surface inboard of the reset surface to thereby automatically pivot the locking member towards the unlocked position and orient the cam member to pass into the slot. The hitch will then continue its sliding movement into the receiver without the need to manually readjust the locking member.

The receiver is further provided with a capture portion such as a recess adjacent the slot into which a portion of the cam member rotates, such as into frictional engagement therewith, when the locking member is pivoted into the locking position. With the hitch seated in the receiver, the capture portion is aligned with the cam member such that rotation thereof brings a portion of the cam member into the capture portion. The hitch will then be locked into the receiver until the locking member is pivoted out of the locked position to thereby release the hitch for movement out of the receiver. While the hitch is locked in the receiver, the support may be moved about without worrying about bumps or other obstacles causing the hitch to prematurely come loose from the receiver. Yet, the locking mechanism does not interfere with sliding the hitch into the receiver in the event the locking member is not in the unlocked position. In accordance with a further aspect of the present invention, the locking member may include one or more spring-loaded arms along one edge which bear against a set plate in the unlocked position of the locking member so as to minimize the risk of the locking member inadvertently coming out of the unlocked position.

Advantageously, the locking member pivots in a plane generally parallel with the path along which the hitch slides into the receiver. The locking member may thus rotate in either a clockwise or counterclockwise direction. The receiver is advantageously provided with a pair of opposed capture portions such that upon rotation of the locking member in either direction out of the unlocking position will bring the cam member portion into one of the capture portions such that the locking member has two locking positions. Further advantageously, the slot is provided with two reset surfaces, each aligned with a respective capture portion, and the cam member has two camming surfaces, such that if the locking member is out of the unlocked position in either direction, one of the camming surfaces engages one of the reset surfaces to automatically realign the cam member for unimpeded entry into the slot so that the hitch can be readily slid into the receiver.

By virtue of the foregoing, there is thus provided a lockable mounting mechanism which is adapted to avoid undesired release of the hitch from the receiver, but which does not interfere with sliding the hitch into the receiver. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention and, together with the general description of the invention given above and the detailed description of the embodiment given below, serve to explain the principles of the present invention.

DETAILED DESCRIPTION OF THE DRAWINGS

Figure 1:
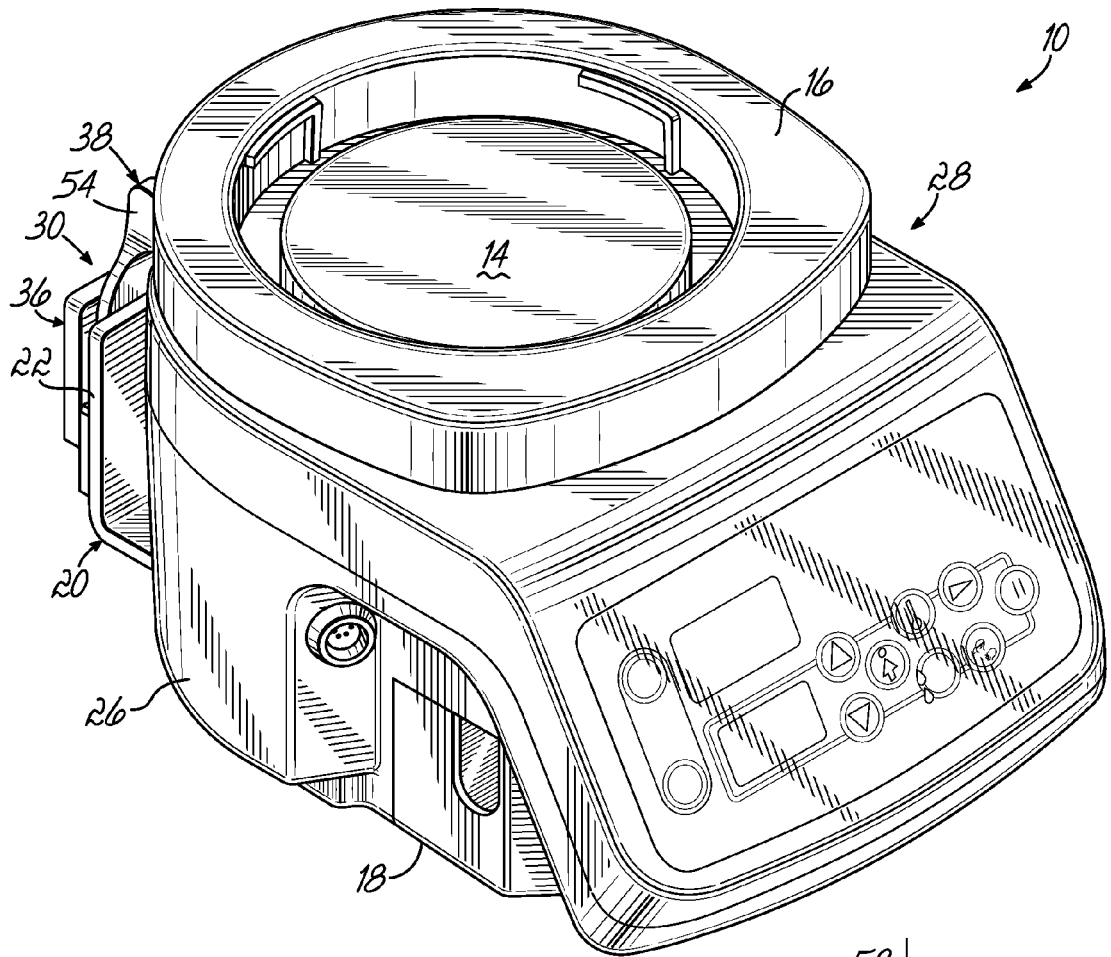
FIG. 1 is a perspective view of an exemplary heater unit incorporating a portion of a lockable mounting mechanism constructed in accordance with the principles of the present invention.

With reference to FIG. 1, there is shown an exemplary respiratory system heater unit 10 for use with the present invention as will be explained below. Heater unit 10 includes a housing 12 containing the electrical and electronic circuitry (not shown) to regulate the temperature of a heated plate 14 supported on housing 12. Heated plate is surrounded by a locking ring 16 adapted to releasably receive a disposable chamber (not shown) in thermal contact with heated plate 14 so as to heat water (not shown) therein for purposes of heating and humidifying breathable gas passing through the chamber and coupled to a patient via a breathing circuit (also not shown). Details of suitable heater units, heated plates, and chambers are shown in U.S. Pat. Nos. 5,943,473 and 6,988, 487; concurrently-filed U.S. patent application Ser. No. 11/927,038; and concurrently-filed U.S. patent application Ser. No. 11/926,982; the disclosures of all four of which are incorporated herein by reference in their respective entireties.

Figure 2A:
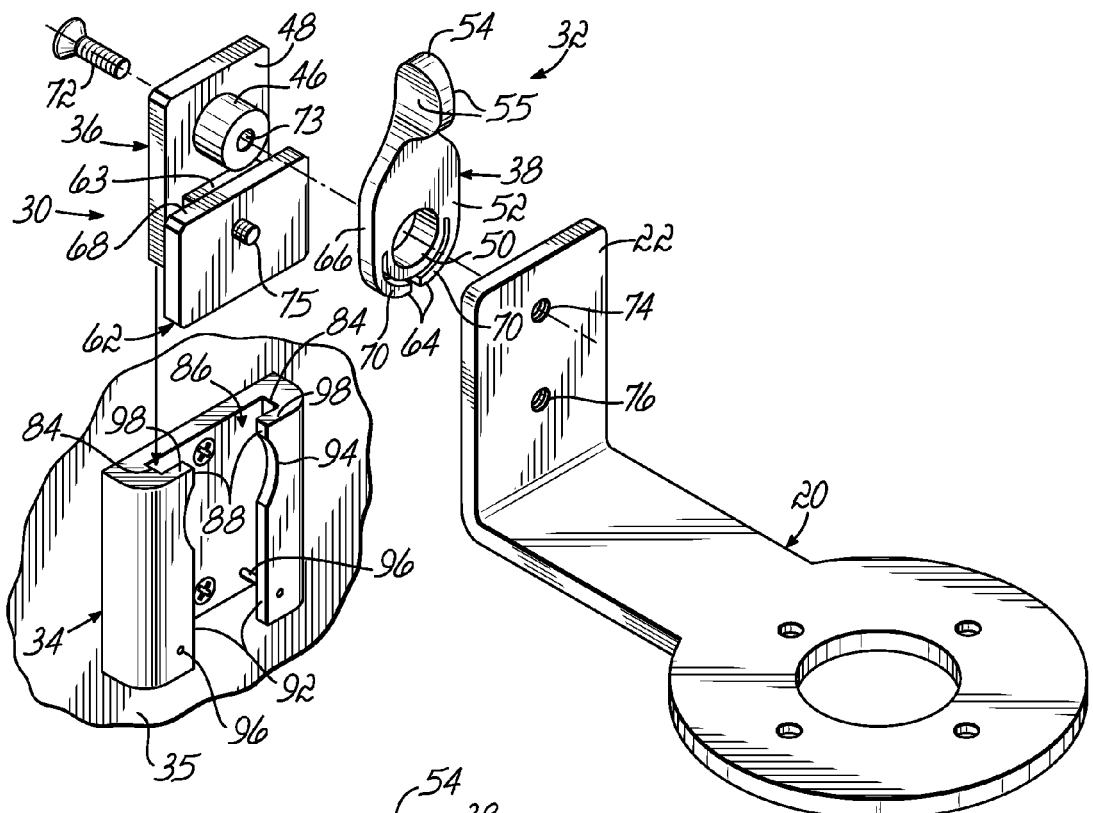
FIGS. 2A-2C are perspective views schematically showing how the lockable mounting mechanism of FIG. 1 is assembled.
Figure 2B:
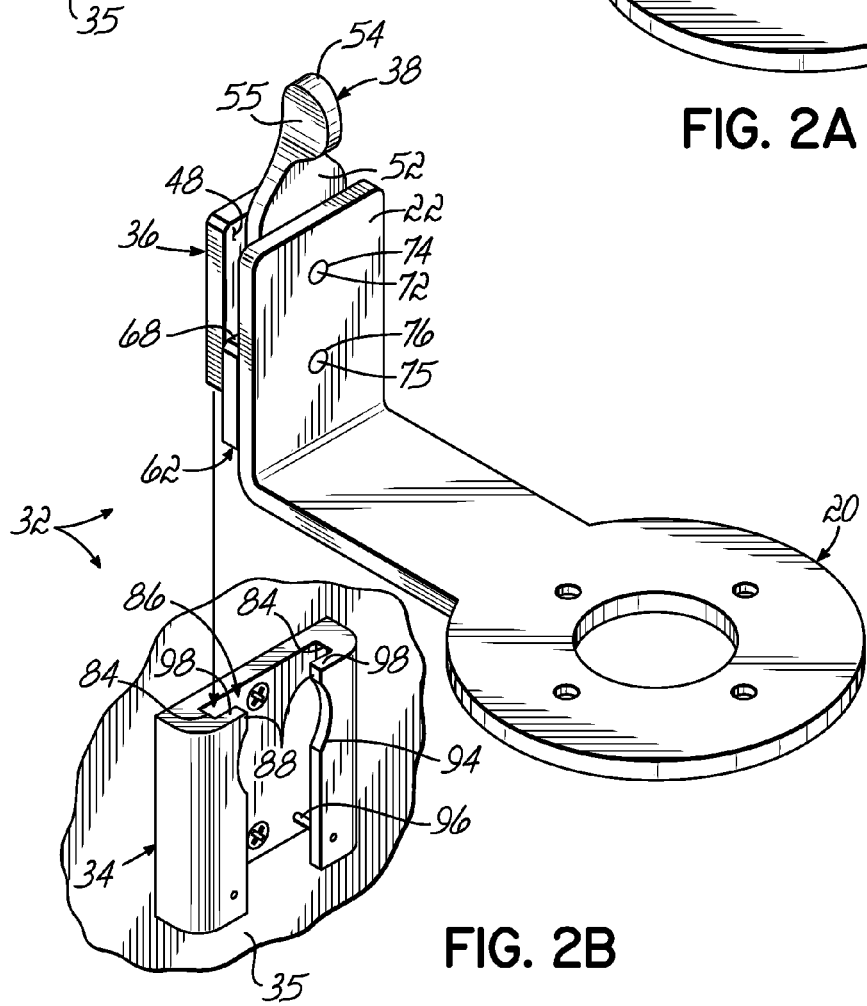
Figure 2C:
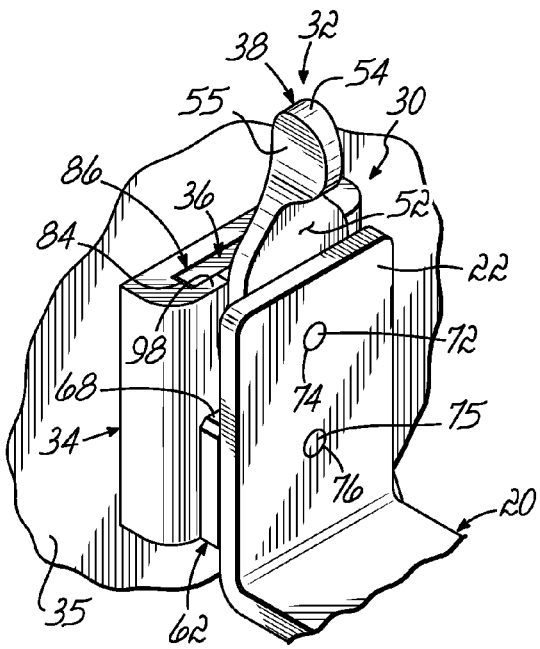

Secured to housing 12, such as to the bottom 18 thereof, is an L-shaped mounting bracket 20 having an arm 22 adjacent the back side 24 of housing 12. Bracket 20 could instead be secured to housing 12 so as to place arm 22 in other positions, such as adjacent the left or right sides 26 or 28 of housing 12. As seen in greater detail in FIGS. 2A through 2C, secured to arm 22 of mounting bracket 20 is a hitch portion 30 of a lockable mounting mechanism 32 adapted to mate with and lock to a receiver portion 34 of mechanism 32. Receiver portion 34 is coupled to a support 35 to which heater unit 10 is to be mounted.

Figure 3A:
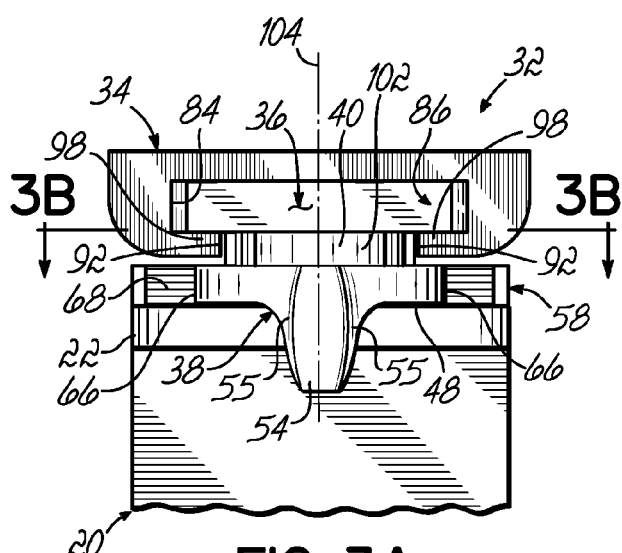
FIG. 3A is a top view showing the lockable mounting mechanism of FIG. 1 after it has been assembled.
Figure 3B:
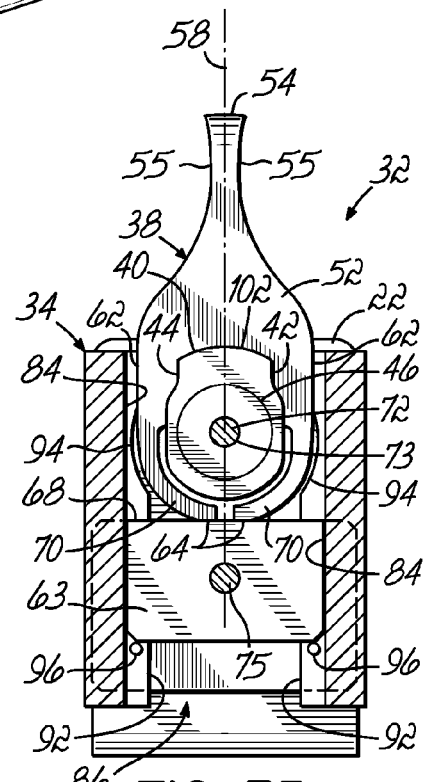
FIG. 3B is a cross-sectional view taken along line 3B-3B of FIG. 3A.
Figures 4A, 4B:
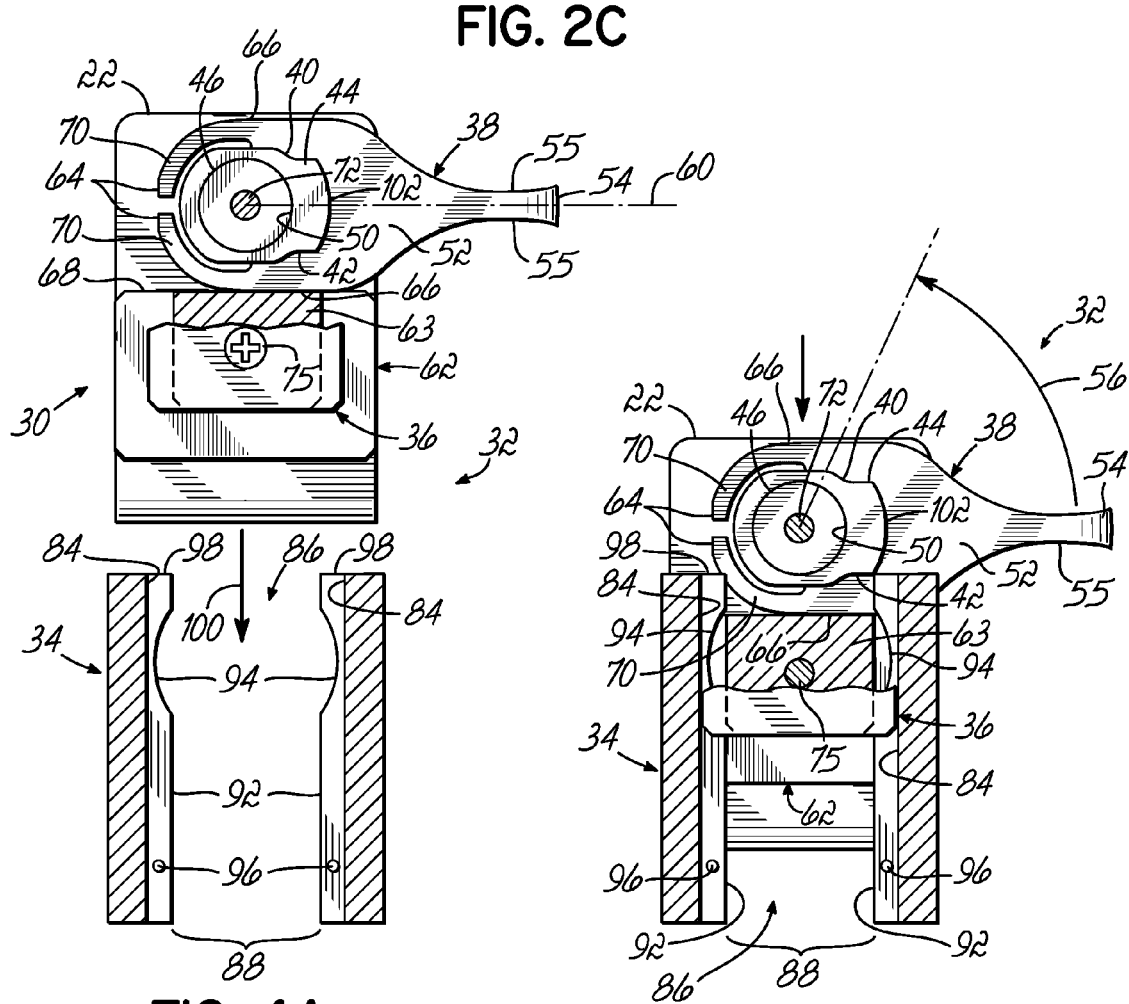
FIGS. 4A-4E are cross-sectional views sequentially showing the operation of the lockable mounting mechanism of FIG. 1.

Hitch portion 30 includes a hitch member 36 with which is associated a pivoting locking member 38 such as a toggle switch adapted to pivot between an unlocked position and one of two locked positions as will be described below. A cam member 40 having first and second camming surfaces 42, 44 (see, e.g., FIGS. 3A and 3B) is associated with locking member 38. Cam member 40 is advantageously rigidly affixed to or formed as part of locking member 38 so as to rotate therewith. In the embodiment shown herein, cam member 40 is disposed between hitch member 36 and locking member 38. Hitch member 36 is generally rectangular in nature and includes a cylindrical neck portion 46 extending outwardly from a face surface 48 of hitch member 36. Locking member 38 and cam member 40 include a bore 50 extending through body portion 52 of locking member 38 and through cam member 40. Bore 50 is sized to be received on neck portion 46 so as to rotatably mount locking member 38 and cam member 40 to neck portion 46 of hitch member 36. Locking member 38 includes an offset grip portion 54 extending from body portion 52 and by which a user (not shown) may pivot locking member 38 between the locked and unlocked positions. Grip portion 54 may incorporate surfaces 55 that are generally transverse to plane of rotation (as along arrows 56 and 57 in FIGS. 4B and 4E) of locking member 38 to provide an easy grip between a person's fingers and thumbs (not shown). In the unlocked position of locking member 38 shown in FIG. 3B by way of example, grip portion 54 extends upwardly along vertical axis 58. Locking member 38 may rotate clockwise or counterclockwise therefrom as along arrow 57 in FIG. 4E into a locked position with grip portion 54 extending along a horizontal axis 60 as seen in FIG. 4A by way of example such that grip portion 54 extends at −90° from the unlocked position as obtained by counterclockwise rotation of locking member 38 (when looking from heater unit 10); counterclockwise rotation would result in the grip portion extending at +90° from the unlocked position.

Hitch portion 30 further includes a set plate 62 coupled to hitch member 36. A spacer 63 is situated between set plate 62 and face 48 of hitch member 36 sized to match the thickness of cam member 40 so as to position locking member 38 to selectively engage set plate 62 in the locked and unlocked positions. Spacer 63 may be integral with face 48, or with set plate 62, or could be a separate component. Locking member 38 has first and second flat unlock position surfaces 64 and first and second flat lock position surfaces 66 situated to confront and engage a flat bearing surface 68 of set plate 62 in the unlocked and locked positions of locking member 38 as seen for example in FIGS. 3B and 4A, respectively. Unlock position surfaces 64 are advantageously formed at the free ends of opposed spring arms 70 integrally formed with and extending below body portion 52 of locking member 38. Spring arms 70 have arcuate profiles and are adapted to resiliently urge unlock position surfaces 64 against bearing surface 68 of set plate 62 in the unlocked position of locking member 38 such that the slight interference fit therebetween generally holds locking member 38 against movement out of the unlocked position. Force applied to locking member 38, such as at surfaces 55 in the direction of arrow 57 (or opposite thereto) sufficient to overcome the interference fit between bearing surface 68 and unlock position surfaces 64 pivots locking member 38 toward one of the locked positions until one of lock position surfaces 66 engages against bearing surface 68.

Referring back to FIGS. 2A-2C, hitch portion 30 is secured to arm 22 of mounting bracket 20 by inserting a fastener 72 through a bore 73 in neck portion 46 to engage a corresponding threaded bore 74 in mounting bracket 20. A second fastener 75 secures hitch member 36 to set plate 62 and further secures hitch portion 30 to arm 22 by engaging a corresponding threaded bore 76 in mounting bracket 20.

Figure 4C:
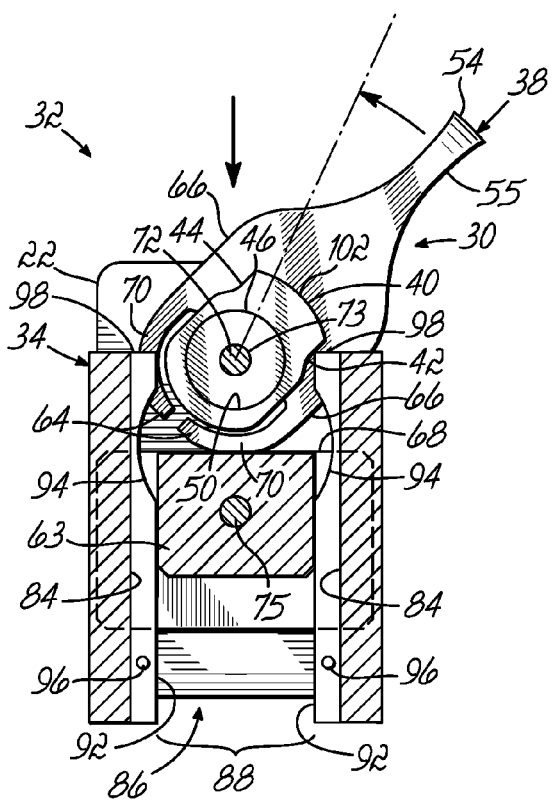
Figure 4D:
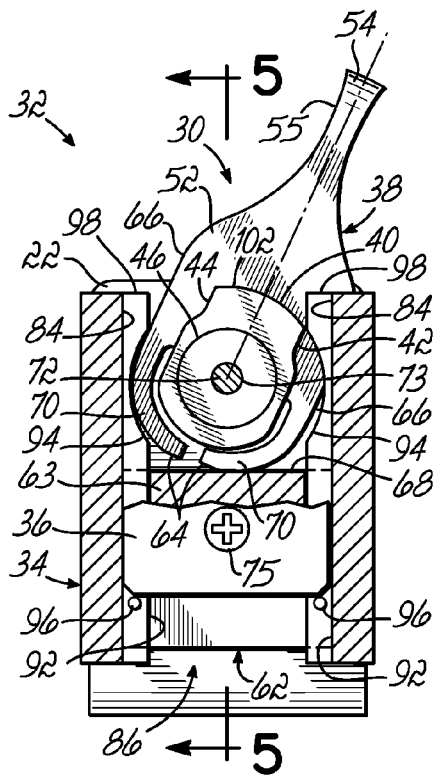
Figure 4E:
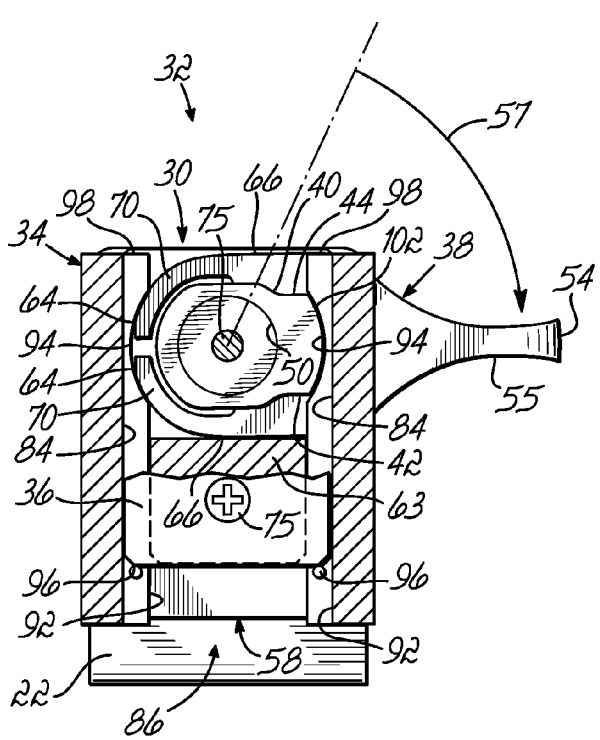
Figure 5:
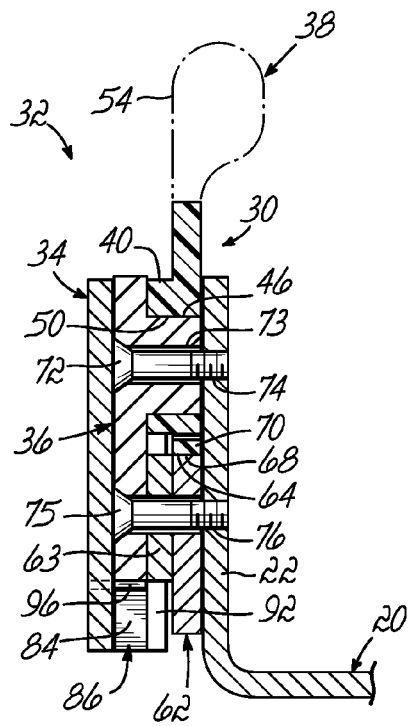
FIG. 5 is a cross sectional view taking along the line 5-5 in FIG. 4D.

Receiver portion 34 defines a keyway 84 with a channel 86 configured to accommodate the hitch member 36 and a longitudinal slot or opening 88 configured to accommodate cam member 40 and spacer 63. Slot 88 is defined by opposed walls 92, at least one of which, but preferably both, has a capture portion 94 formed therein. Stopping pins 96 are positioned in the keyway 84 below the capture portion 94 to prevent the hitch member 36 from sliding all the way through the channel 86. As can be seen in FIG. 3B, when locking member 38 is in the locked position, cam member 40 is sized to fit between walls 92 with camming surface 42 and 44 inboard of walls 92 so as to easily slide down through slot 88. However, if locking member 38 is not in the unlocked position, such as with locking member 38 in a locked position or between a locked and the unlocked position, as seen in FIGS. 4B and 4C, cam member 40 is rotated sufficiently that a camming surface 42 (or 44) is outboard of a wall 92 and the respective top or reset surface 98 thereof over capture portion 94. If one were to attempt to slide hitch member 36 into channel 86, camming surface 42 or 44 would impinge or engage against a respective reset surface 98. The engaged camming surface (42 or 44) and respective reset surface 98 cooperate such that continued sliding of hitch member 36 into channel 86 will cause cam member 40 to rotate to bring the camming surface (42 or 44) inboard of respective wall 92 and its reset surface 98, to thereby automatically pivot locking member 38 toward the unlocked position. As a consequence, hitch member 36 may be slid all the way into channel 86 (as along arrow 100 in FIG. 4A) until it engages stopping pins 96. Thereafter, locking member 38 may be pivoted to bring an upper arcuate edge portion 102 of cam member 40 into a capture position 94 as seen in FIG. 4E whereat hitch portion 30 is locked to receiver portion 34.

FIGS. 4A through 4E illustrate the operation of lockable mounting mechanism 32 in further detail. Rather than initially being set in the unlocked position, however, for illustrative purposes locking member 38 is shown in the locked position before hitch member 36 is inserted into the channel 86. When hitch member 36 is inserted into channel 86 and pushed downwardly (along arrow 100 in FIG. 4A) one of camming surfaces 42 or 44 engages a respective reset surface 98 of one of opposed walls 92 (FIG. 4B) and causes rotation of locking member 38 toward the unlocked position (FIG. 4C). The resulting contact force is also sufficient to counteract the biasing force created by one of spring arms 70 as the arm comes into contact with bearing surface 68. Continued downward movement of hitch member 36 eventually causes locking member 38 and cam member 40 to rotate toward the unlocked position sufficient to allow cam member 40 to be received in the slot 88 such that hitch member 36 may be slid all the way into channel 86 without interrupting the user or having to manually adjust locking member 38.

When hitch member 36 contacts stopping pins 96, cam member 40 is aligned with capture portion 94 such that manual rotation of locking member 38 as along arrow 57 in FIG. 4B brings edge 102 into frictional engagement with capture portion 94 to thus secure or lock hitch portion 30 to receiver portion 34. That interference fit, alone or in combination with the spring arm biasing force that must be overcome to rotate the locking member 38 back towards the unlocked position, secures hitch portion 30 in receiver portion 34. With hitch portion 30 thus locked in receiver portion 34, movement of support 35 will not tend to cause premature or unexpected release of hitch member 30 therefrom. Hence, heater unit 10 is reliably secured to support 36. To allow locking member 38 to rotate clockwise or counterclockwise from the unlocked position to a locked position, hitch portion 30 and receiver portion 34 are symmetric about a center plane 104 (FIG. 3A). If it is decided to release heater unit 10 from support 35, locking member is manually rotated as along arrow 56 in FIG. 4B to rotate edge 102 out of capture portion 94 as locking member 38 is brought into the unlocked position. Hitch member 36 is then free to be slid back out of channel 86 to disconnect heater unit 10 from support 35.

In use, hitch portion 30 is secured to mounting bracket 20 on heater unit 10 and receiver portion 34 is secured to support 36 such as a ventilator, pole or other object. A practitioner (not shown) may then quickly position the heater unit 10 and insert the hitch member 36 into the channel 86 without taking the time to make sure that the locking member 38 is first in the unlocked position. Instead, hitch member 36 may simply be slid into channel 86 and if locking member 38 is out of the unlocked position, camming surface 42 or 44 and a respective reset surface 98 will cooperate to automatically rotate locking member 38 toward the unlocked position as to allow hitch member 36 to readily slide all the way into channel 86. Thereafter, locking member 38 may be rotated in either a clockwise or counterclockwise direction to engage the cam member 40 with a respective capture portion 94. As there is no need to worry about which way to manipulate locking member 38, lockable mounting mechanism 32 is easy to use in the field.

By virtue of the foregoing, there is thus provided a lockable mounting mechanism which is adapted to avoid undesired release of the hitch from the receiver, but which does not interfere with sliding the hitch into the receiver.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, the cam member 40 may be coupled to the locking member 38 in a different location such that it is not aligned along the same axis of rotation as the locking member 38. Also, camming surfaces 42 and 44 and locking edge 102 could be found on body portion 52 of locking member 38 and cam member 40 and spacer 63 dispensed with. Further, while reset surfaces 98 are shown as being horizontally extending surfaces, they could be angled or even defined along an edge such as at the corner adjacent slot 88. Also, while two unlock position surfaces 64 and two springs arms 70 are shown only one of either or both may be provided. Additionally, if desired, locking member 38 could be limited in its motion to rotate from the unlocked to the locked position in only a clockwise or only a counterclockwise direction, in which even only one lock position surface 66 and one capture portion 94 may be necessary. Moreover, while the lockable mounting mechanism 32 has been described in the context of mounting heater unit 10 of a respiratory system to a support 35, a lockable mounting mechanism constructed according the principles of the present invention may be utilized in a wide variety of other applications in which it is desired to secure a first object to a second object. The invention in its broader aspects is therefore not limited to the specific details, representative apparatus and method, and illustrative examples shown and described. Accordingly, departures may be made from such details without departing from the spirit or scope of the general inventive concept.

Having described the invention, what is claimed is:

1. A lockable mounting mechanism comprising:
    a hitch portion and a separate receiver portion;
    the hitch portion having a hitch member, a locking member being rotatable in a plane parallel to the hitch member between an unlocked position and a locked position, and a camming surface being rotatable with the locking member;
    the receiver portion having a channel, the hitch member of the hitch portion and the channel of the receiver portion sized to slidably receive the hitch member into the channel whereby to mount the hitch portion to the receiver portion, the receiver portion further having a reset surface positioned to engage the camming surface as the hitch member is slid into the channel when the locking member is out of the unlocked position, the camming surface and reset surface cooperating to automatically rotate the locking member toward the unlocked position as the hitch member is slid into the channel.

2. The lockable mounting mechanism of claim 1, the hitch portion further having a cam member rotatable with the locking member, the camming surface being on the cam member.

3. The lockable mounting mechanism of claim 2, the camming surface being inboard of the reset surface in the unlocked position of the locking member.

4. The lockable mounting mechanism of claim 1, the camming surface being inboard of the reset surface in the unlocked position of the locking member.

5. The lockable mounting mechanism of claim 1, the hitch portion including a set plate, the locking member selectively engaging the set plate.

6. The lockable mounting mechanism of claim 5, the locking member including at least one spring arm positioned to resiliently engage the set plate in the unlocked position of the locking member.

7. A lockable mounting mechanism comprising:
a hitch portion and a separate receiver portion;
the hitch portion having a hitch member, a locking member being rotatable between an unlocked position and a locked position, and a camming surface being rotatable with the locking member, the hitch portion further having a cam member rotatable with the locking member, the camming surface being on the cam member;
the receiver portion having a channel, the hitch member of the hitch portion and the channel of the receiver portion sized to slidably receive the hitch member into the channel whereby to mount the hitch portion to the receiver portion, the receiver portion further having a reset surface positioned to engage the camming surface as the hitch member is slid into the channel when the locking member is out of the unlocked position, the camming surface and reset surface cooperating to automatically rotate the locking member toward the unlocked position as the hitch member is slid into the channel, the cam member having a portion which engages the capture portion in the locked position of the locking member with the hitch member in the channel.

8. A lockable mounting mechanism comprising:
a hitch portion and a separate receiver portion;
the hitch portion having a hitch member, a locking member being rotatable between an unlocked position and a locked position, and a camming surface being rotatable with the locking member;
the receiver portion having a channel, the hitch member of the hitch portion and the channel of the receiver portion sized to slidably receive the hitch member into the channel whereby to mount the hitch portion to the receiver portion, the receiver portion further having a reset surface positioned to engage the camming surface as the hitch member is slid into the channel when the locking member is out of the unlocked position, the camming surface and reset surface cooperating to automatically rotate the locking member toward the unlocked position as the hitch member is slid into the channel, the receiver portion including a slot, the cam member of the hitch portion and the slot being sized to receive the cam member in the slot.

9. The lockable mounting mechanism of claim 8, the slot being defined between a pair of opposed walls of the receiver portion, the reset surface being defined along an edge of one of the opposed walls, the camming surface being inboard of the reset surface in the unlocked position of the locking member.

10. The lockable mounting mechanism of claim 8, the receiver portion including a capture portion defined along the slot, the cam member having a portion engaging the capture portion in the locked position of the locking member with the hitch member in the channel.

11. A lockable mounting mechanism comprising:
a hitch portion and a separate receiver portion;
the hitch portion having a hitch member, a locking member being rotatable between an unlocked position and a locked position, and a camming surface being rotatable with the locking member, the hitch portion including a set plate, the locking member selectively engaging the set plate;
the receiver portion having a channel, the hitch member of the hitch portion and the channel of the receiver portion sized to slidably receive the hitch member into the channel whereby to mount the hitch portion to the receiver portion, the receiver portion further having a reset surface positioned to engage the camming surface as the hitch member is slid into the channel when the locking member is out of the unlocked position, the camming surface and reset surface cooperating to automatically rotate the locking member toward the unlocked position as the hitch member is slid into the channel, the locking member including at least one unlock position surface and at least one lock position surface, the unlock position surface positioned to engage the set plate in the unlocked position of the locking member, the lock position surface positioned to engage the set plate in the locked position of the locking member.

12. The lockable mounting mechanism of claim 11, the locking member including at least one spring arm supporting the unlock position surface, the spring arm positioned to resiliently engage the set plate in the unlocked position of the locking member.

13. A lockable mounting mechanism comprising:
a hitch portion and a separate receiver portion;
the hitch portion having a hitch member, a locking member being rotatable between an unlocked position and first and second locked positions, and first and second camming surfaces being rotatable with the locking member;
the receiver portion having a channel, the hitch member of the hitch portion and the channel of the receiver portion sized to slidably receive the hitch member into the channel whereby to mount the hitch portion to the receiver portion, the receiver portion further having first and second reset surfaces positioned to respectively engage the first and second camming surfaces as the hitch member is slid into the channel when the locking member is out of the unlocked position toward one of the first and second locked positions, the engaging camming surface and reset surface cooperating to automatically rotate the locking member toward the unlocked position as the hitch member is slid into the channel.

14. The lockable mounting mechanism of claim 13, the hitch portion further having a cam member rotatable with the locking member, the camming surfaces being on the cam member.

15. The lockable mounting mechanism of claim 14, the receiver portion including a slot, the cam member of the hitch portion and the slot being sized to receive the cam member in the slot.

16. The lockable mounting mechanism of claim 15, the slot being defined between first and second opposed walls of the receiver portion, the respective first and second reset surfaces being defined along respective edges of the first and second opposed walls, the camming surfaces being inboard of the reset surfaces in the unlocked position of the locking member.

17. The lockable mounting mechanism of claim 15, the receiver portion including first and second capture portions defined along opposite aspects of the slot, the cam member having a portion engaging a respective one of the capture portions in a respective one of the locked positions of the locking member with the hitch member in the channel.

18. The lockable mounting mechanism of claim 14, the camming surfaces being inboard of the reset surfaces in the unlocked position of the locking member.

19. The lockable mounting mechanism of claim 14, the receiver portion including first and second capture portions, the cam member having a portion engaging a respective one of the capture portions in a respective one of the locked positions of the locking member with the hitch member in the channel.

20. The lockable mounting mechanism of claim 13, the camming surfaces being inboard of the reset surfaces in the unlocked position of the locking member.

21. The lockable mounting mechanism of claim 13, the hitch portion including a set plate, the locking member selectively engaging the set plate.

22. The lockable mounting mechanism of claim 21, the locking member including a pair of unlock position surfaces and a pair of lock position surfaces, the unlock position surfaces positioned to engage the set plate in the unlocked position of the locking member, respective ones of the lock position surfaces positioned to engage the set plate in respective ones of the locked positions of the locking member.

23. The lockable mounting mechanism of claim 22, the locking member including a pair of spring arms each supporting a respective one of the unlock position surfaces, the spring arms positioned to resiliently engage the set plate in the unlocked position of the locking member.

24. The lockable mounting mechanism of claim 21, the locking member including a pair of spring arms positioned to resiliently engage the set plate in the unlocked position of the locking member.

25. A method of securing a first object to a second object comprising:
inserting a hitch member of a hitch portion coupled to the first object into a channel of a receiver portion coupled to the second object, the hitch portion having a locking member being rotatable in a plane parallel to the hitch member between an unlocked position and a locked position; and
automatically rotating the locking member in the plane toward the unlocked position by cooperation of a camming surface of the hitch portion and a reset surface of the receiver portion if the locking member is out of the unlocked position as the hitch member is being inserted into the channel.

\* \* \* \* \*